United States Patent [19]

Tovey

[11] Patent Number: 5,405,360
[45] Date of Patent: Apr. 11, 1995

[54] RESILIENT ARM MESH DEPLOYER

[75] Inventor: H. Jonathan Tovey, Milford, Conn.

[73] Assignee: United States Surgical Corporation, Norwalk, Conn.

[21] Appl. No.: 96,059

[22] Filed: Jul. 22, 1993

Related U.S. Application Data

[63] Continuation of Ser. No. 840,386, Feb. 24, 1992, abandoned.

[51] Int. Cl.⁶ ............................................. A61B 17/00
[52] U.S. Cl. .................................................... 606/151
[58] Field of Search ................ 128/117.1; 604/59, 61; 606/1, 108, 110, 113, 127, 151, 140–142, 213; 623/66

[56] References Cited

U.S. PATENT DOCUMENTS

| | | |
|---|---|---|
| 30,471 | 10/1860 | Dudley ................................. 606/127 |
| 460,940 | 10/1891 | Baugh . |
| 736,744 | 8/1903 | Kratzmueller . |
| 870,021 | 11/1907 | Duffee . |
| 2,767,703 | 10/1956 | Nieburgs . |
| 3,525,339 | 8/1970 | Halligan . |
| 3,540,431 | 11/1970 | Mobin-Uddin . |
| 3,811,446 | 5/1974 | Lerwick et al. . |
| 3,874,388 | 4/1975 | King et al. ........................... 606/213 |
| 3,938,527 | 2/1976 | Rioux et al. . |
| 4,174,715 | 11/1979 | Hasson ................................. 606/127 |
| 4,190,042 | 2/1980 | Sinnreich . |
| 4,425,908 | 1/1984 | Simon . |
| 4,467,802 | 8/1984 | Maslanka ............................ 606/127 |
| 4,557,255 | 12/1985 | Goodman . |
| 4,654,028 | 3/1987 | Suma . |
| 4,655,219 | 4/1987 | Petruzzi . |
| 4,732,150 | 3/1988 | Keener, Jr. . |
| 4,744,364 | 5/1988 | Kensey ................................. 606/213 |
| 4,807,626 | 2/1989 | McGirr . |
| 4,832,055 | 5/1989 | Palestrant . |
| 4,909,789 | 3/1990 | Tagushi et al. . |
| 4,917,089 | 4/1990 | Sideris . |
| 4,926,860 | 5/1990 | Stice et al. ........................... 606/213 |
| 4,955,889 | 9/1990 | Van Gent . |
| 5,021,059 | 6/1991 | Kensey et al. ....................... 606/213 |
| 5,061,274 | 10/1991 | Kensey ................................. 606/213 |
| 5,064,435 | 11/1991 | Porter . |
| 5,069,226 | 12/1991 | Yamauchi et al. .................. 604/281 |
| 5,080,088 | 1/1992 | LeVahn . |
| 5,109,830 | 5/1992 | Cho ...................................... 604/281 |
| 5,116,357 | 5/1992 | Eberbach ............................ 606/151 |
| 5,122,155 | 6/1992 | Eberbach ............................ 606/213 |
| 5,133,721 | 7/1992 | Angulo ................................ 606/78 |
| 5,147,374 | 9/1992 | Fernandez . |
| 5,171,314 | 12/1992 | Dulebohn ............................ 606/113 |
| 5,176,692 | 1/1993 | Wilk et al. . |

FOREIGN PATENT DOCUMENTS

| | | |
|---|---|---|
| 0027704 | 4/1981 | European Pat. Off. ............ 606/113 |
| 0364420 | 4/1990 | European Pat. Off. . |
| 0525791 | 2/1993 | European Pat. Off. . |
| 2567405 | 7/1984 | France . |
| 2741910 | 3/1978 | Germany ............................ 606/141 |
| 2822603 | 11/1979 | Germany . |
| 9102493 | 3/1991 | WIPO . |

OTHER PUBLICATIONS

Surgical Laparoscopy & Endoscopy vol. 1, No. 3, pp. 151-155, Raven Press, Ltd. (1991).

*Primary Examiner*—Stephen C. Pellegrino
*Assistant Examiner*—Glenn Dawson

[57] ABSTRACT

An apparatus is disclosed for positioning surgical implants adjacent to body tissue. The apparatus includes a delivery device having a plurality of delivery arms positioned at the distal end of an elongated rod, and a surgical implant releasably secured to the delivery arms by a securing device. The invention also provides a method for positioning surgical implants adjacent to body tissue.

20 Claims, 7 Drawing Sheets

RESILIENT ARM MESH DEPLOYER

This is a continuation of application Ser. No. 07/840,386, filed on Feb. 24, 1992, now abandoned.

BACKGROUND OF THE INVENTION

1. Field of the Invention

The present invention relates to an apparatus and method for positioning surgical implants adjacent to body tissue to facilitate the fastening of the implant to the body tissue. More particularly, this invention relates to a delivery device having a plurality of delivery arms for endoscopically positioning surgical implants.

2. Description of the Related Art

Hernias are abnormal protrusions of an organ or other body structure through a defect or natural opening in a covering membrane, muscle or bone. An inguinal hernia is a protrusion which makes its way through the abdomen in the inguinal (groin) region. Hernias may be divided into three general classes: direct inguinal hernia, indirect inguinal hernia and femoral hernia. In both a direct and indirect inguinal hernias, a part of the intestine may protrude through a defect (opening or tear) in the supporting abdominal wall to form a hernial sac. In a femoral hernia, a portion of the intestine is forced through the femoral ring into the femoral canal forming a hernial sac.

Hernia repair typically requires surgery which generally includes an incision in the groin ranging up to six inches in length. Several layers of the abdominal wall are generally separated to reach the herniated portions. During the procedure, the opening or tear in the abdominal wall is closed in a manner which resembles the tying of a sack at the neck. Often a surgical mesh is attached by sutures directly over the repaired hernia opening to provide a reinforcement to the opening.

Traditionally, such hernia repairs involved major invasive surgical procedures which often caused excessive trauma to the patient and necessitated unusually long postoperative recuperative periods. In addition, numerous complications, related directly or indirectly to the surgery often resulted, including bleeding, infection, testicular atrophy, organ damage, nerve damage, blood vessel damage, etc. Further, cutting through the numerous layers of tissue to obtain access to the herniated area often caused severe trauma to the patient. A detailed discussion of traditional hernia repair may be found in "Hernia Repair Without Disability, Second Edition", by Irving L. Lichtenstein. Such invasive surgical procedures have also been utilized in other areas of the body, including surgery on the gall bladder, appendix, lungs and the like.

To avoid many of the previously stated risks and problems, the use of laparoscopic and endoscopic surgical procedures have been relatively popular and have provided additional incentive to develop the procedures further. In laparoscopic procedures, surgery is performed in the interior of the abdomen through a small incision. Similarly, in endoscopic procedures, surgery is performed in any hollow viscus of the body through narrow endoscopic tubes inserted through small entrance wounds in the skin.

Laparoscopic and endoscopic procedures generally require that the surgical region be insufflated. Accordingly, any instrumentation inserted into the body must be sealed to ensure that gases do not enter or exit the body through the incision. Moreover, laparoscopic and endoscopic procedures often require the surgeon to act on organs, tissues and/or vessels far removed from the incision. Thus, instruments used in such procedures are typically long and narrow while being functionally controllable from a proximal end of the instrument.

In hernia surgery, as compared to gall bladder surgery, certain procedures and instruments are the same, and certain instrument requirements differ. For example, in hernia surgery a suitable mesh material is generally sutured over the opening in the tissue. Often, the mesh material is attached by sutures and left within the body to act as a reinforcing agent for tissue regrowth in the area of the surgery. One example of a mesh material currently utilized in hernia surgery includes a polypropylene material marketed by C. R. Bard, under the trademark MARLEX. Another example of a mesh material is a tri-fluoroethylene material marketed by W. L. Gore & Associates, Newark, Delaware, under the trademark GORE-TEX.

As noted, during conventional invasive surgical procedures, such mesh materials are manually placed over the defect in the abdominal wall and are often sutured within the surgical opening by conventional suturing techniques. However, with the advent of laparoscopic surgery the need for suitable mesh, mesh positioning and mesh attachment techniques through the relatively narrow endoscopic tubes or cannulas is clearly defined. Up to the present, such devices and techniques for mesh positioning have not yet been developed.

Heretofore, resilient umbrella type devices or extractors have been provided to remove objects from body tissue. Exemplary of these devices is U.S. Pat. No. 4,557,255 to Goodman. Goodman discloses a purse-like surgical net which is operable for retrieving stones and the like from within the human body.

U.S. Pat. No. 4,190,042 to Sinnreich discloses a resilient surgical retractor which in an unstressed condition forms a hook-like appendage at the distal end of the retractor.

However, there remains a need for apparatus which facilitates the endoscopic positioning of surgical implants adjacent to body tissue. In addition to the above apparatus, the present invention relates to a method for positioning surgical implants adjacent to body tissue for stapling.

SUMMARY OF THE INVENTION

The present invention relates to apparatus for positioning surgical implants adjacent to body tissue. More particularly, the apparatus of the present invention comprises a delivery device having a plurality of delivery arms positioned at a distal end of an elongated rod and a securing device for securing a surgical implant to the delivery arms. The present invention also provides a method for positioning surgical implants adjacent to body tissue, comprising the steps of releasably securing a surgical implant to a delivery device having retaining means positioned at a distal end thereof, positioning the surgical implant and the delivery device adjacent to body tissue, and releasing the surgical implant from the delivery device by removing the securing device.

BRIEF DESCRIPTION OF THE DRAWINGS

Preferred embodiments of the invention are described hereinbelow with reference to the drawings wherein.

DETAILED DESCRIPTION OF THE PREFERRED EMBODIMENTS

Generally, the apparatus of the present invention may be adapted for conventional or endoscopic surgical procedures. Therefore, discussions relating to the proximal end of the apparatus or elements of the apparatus refer to end closest to the surgeon. Similarly, the distal end of the apparatus or elements of the apparatus refers to the end furthest from the surgeon.

Figure 1:
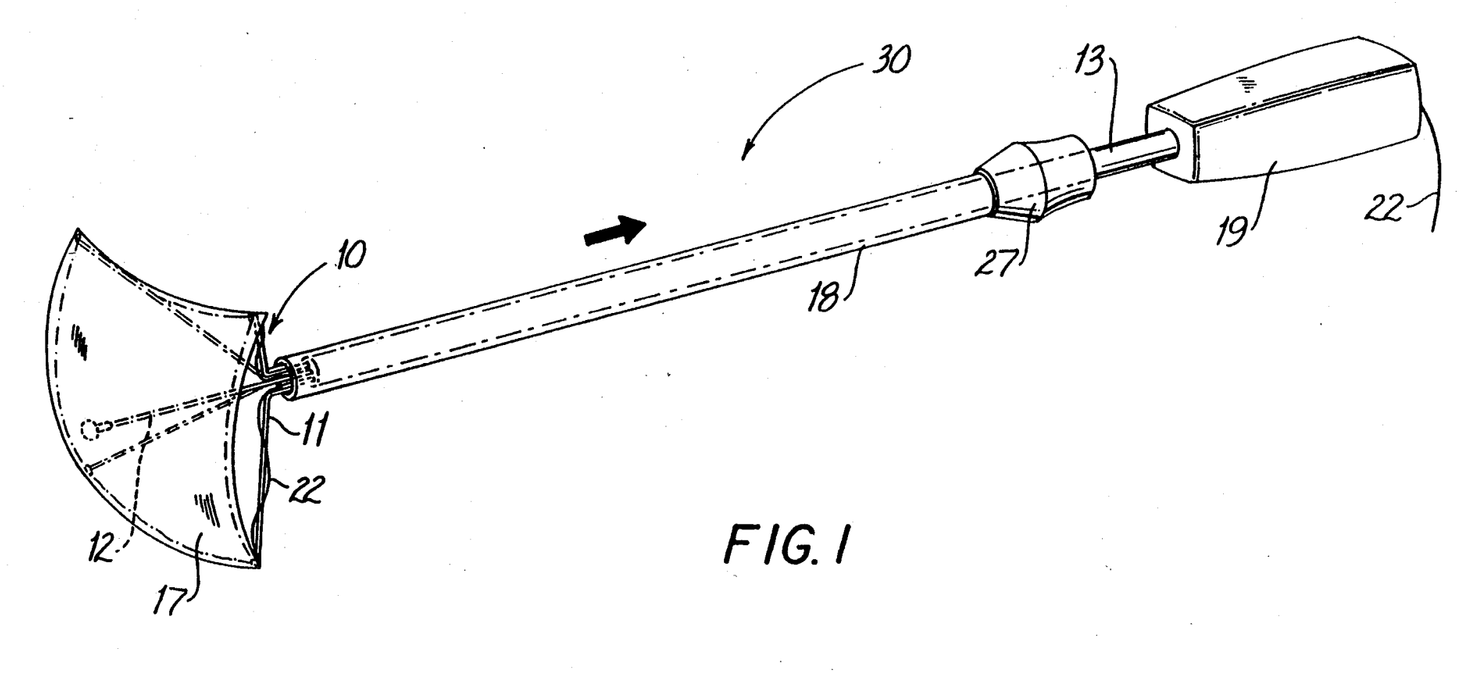
FIG. 1 is a perspective view of a preferred endoscopic implant delivery device illustrating a reciprocating tubular structure enclosing a delivery device having a solid implantable sheet material secured thereto.
Figure 2:
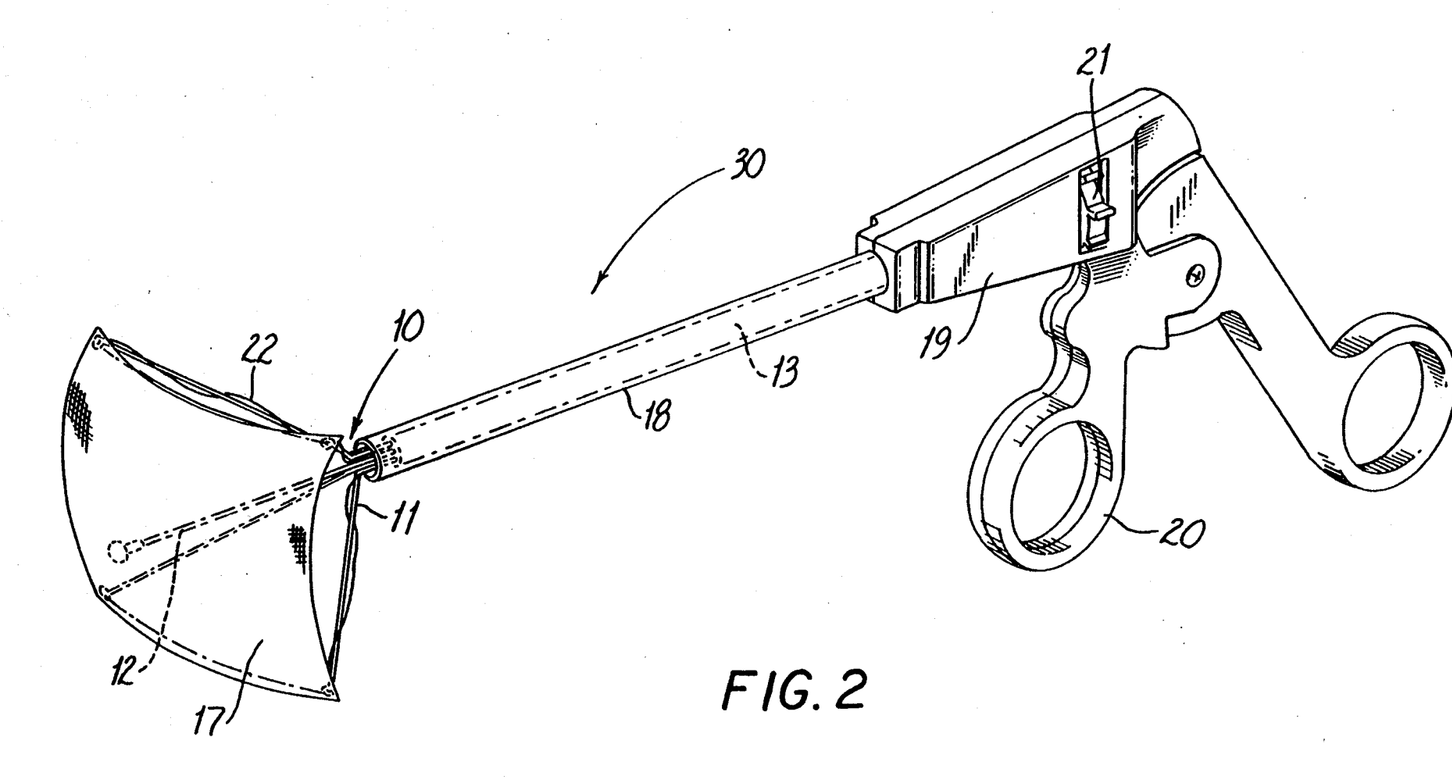
FIG. 2 is a perspective view of another preferred endoscopic implant delivery device illustrating a delivery device having a mesh implantable sheet material secured thereto.

Referring to FIG. 1, the apparatus 30 of the present invention comprises a delivery device, generally indicated by the numeral 10, having a plurality of delivery arms 11 positioned at a distal end of an elongated rod 13, and a securing device 22 for securing a surgical implant 17 to the delivery arms 11. In addition, the apparatus of the present invention may further comprise an endoscopic portion 18 and a handle assembly 19 as illustrated in FIGS. 1 and 2.

The surgical implant may be an implantable sheet material configured in a variety of shapes or forms. For example, the implantable sheet material may be flat, ball-shaped, cylindrically or tubularly rolled, as well as any other configurations within the knowledge of those skilled in the art. In addition, the implantable sheet material may be a solid sheet, shown in FIG. 1, a mesh-like sheet, shown in FIG. 2, having a variety of weave configurations or any combination thereof. For example, the implantable sheet material may have a solid inner configuration and a mesh outer configuration. Alternately, the implantable sheet material may have a mesh inner configuration which is tightly woven and a mesh outer configuration which is loosely woven. While the surgical implant may be discussed as a surgical mesh, the surgical implant embodies a wide variety of configurations, as discussed above. Furthermore, the use of the term "surgical mesh" or "mesh" is not intended to limit the types of implants which may be used in the present invention.

Figures 3, 4:
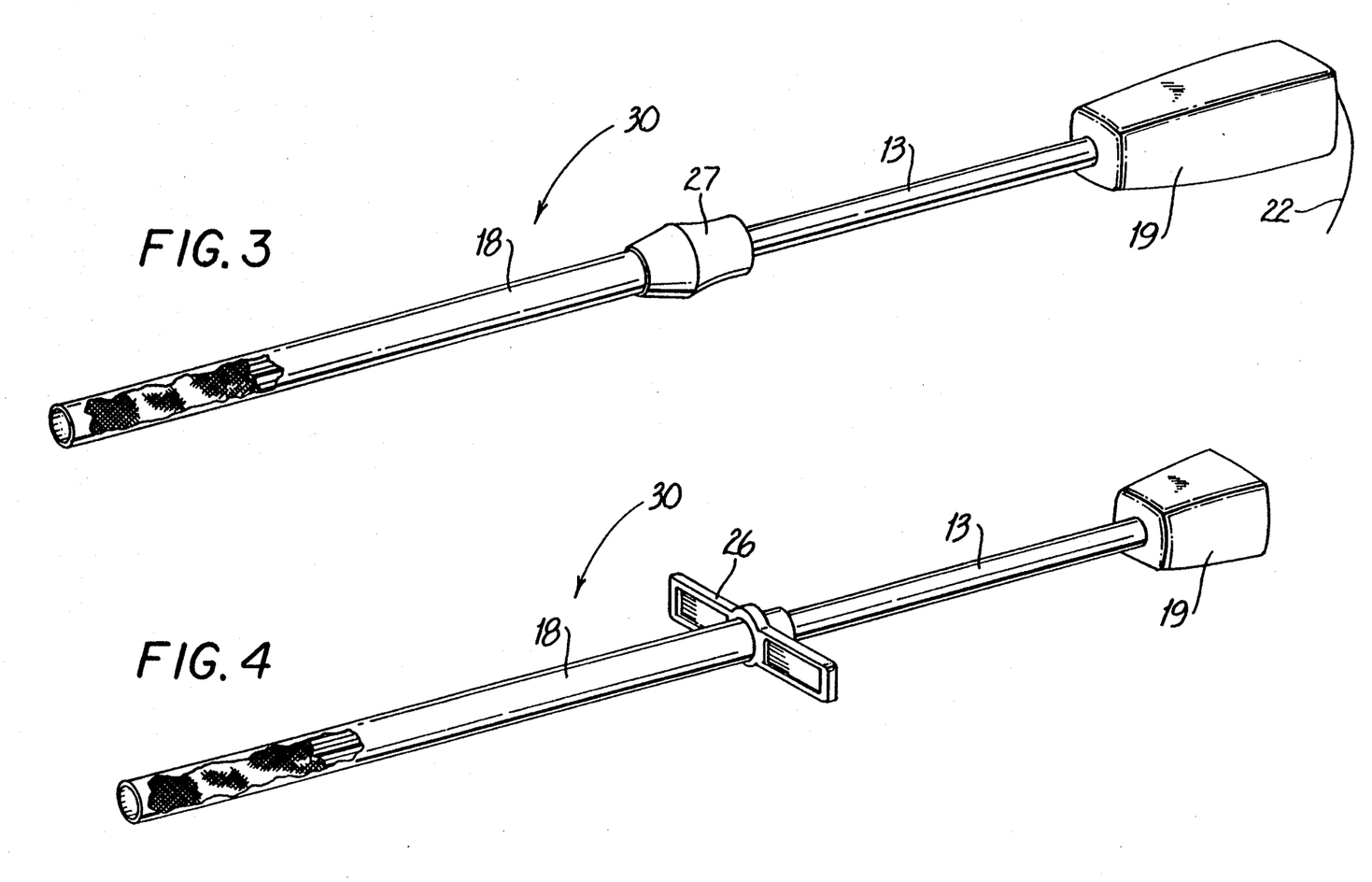
FIG. 3 is a perspective view of the preferred endoscopic implant delivery device of FIG. 1 in a retracted position.
FIG. 4 is a perspective view of an alternate embodiment of the endoscopic implant delivery device.

In a preferred embodiment shown in FIGS. 1 and 3, the endoscopic portion 18 reciprocates along the longitudinal axis of the rod 13 so as to retract or extend the surgical mesh. It is also preferred that the proximal end of the endoscopic portion 18 have a gripping means 27 secured thereto, which facilitates the reciprocating movement of the endoscopic portion 18 relative to the longitudinal axis of the elongated rod 13. As an illustration, the surgeon may reciprocate the endoscopic portion 18 by holding the gripping means 27 in one hand and the handle assembly 19 in the other, sliding the endoscopic portion 18 along the rod 13 causing the delivery arms 11 to extend from or retract into the distal end of the endoscopic portion 18.

Preferably, the gripping means is a substantially conically shaped knob 27, as shown in FIG. 1. However, the gripping means may be in any form so long as it facilitates the reciprocal movement of the endoscopic portion 18 relative to the longitudinal axis of the elongated rod 13. For example, the gripping means may be barrel, disk or mushroom shaped member, as well as any irregular shaped member. Additionally, a grip enhancing means may be formed on or attached to the gripping means. The grip enhancing means may be in the form of protrusions extending from the gripping means or knurling formed on the gripping means, which allows the surgeon to firmly grasp the gripping means.

In an alternate embodiment, the proximal end of the endoscopic portion 18 is distally connected to the handle assembly 19, as shown in FIG. 2. The elongated rod 13 is extended through the endoscopic portion 18 and operatively connected to the trigger means 20 which is pivotally secured to the handle assembly 19. Actuation of the trigger means 20, selectively causes longitudinal distal movement of the elongated rod 13 causing the delivery arms 11 to retract into or extend from the endoscopic portion 18. Generally, the handle assembly 19 may be configured in any shape or form which can be manipulated during surgery. The handle assembly 19 may further include a rotation means 21, allowing the surgeon to rotate the delivery arms and pusher rod.

In still another embodiment, the elongated rod extends coaxially through the endoscopic portion and reciprocates within the endoscopic portion so as to retain and extend the surgical mesh. The proximal end of the rod has a handle assembly 19 connected thereto and the proximal end of the endoscopic portion 18 has finger gripping means 26 secured thereto, as illustrated in FIG. 4. This configuration allows the surgeon to apply pressure to the handle assembly along the elongated rod's longitudinal axis with at least one finger and to firmly grasp the finger gripping means with the remaining fingers, thereby causing the elongated rod to reciprocate within the endoscopic portion. The finger gripping means may be arcuate, straight, circular or elliptical members which allow the surgeon to grasp the members with his or her fingers.

Endoscopic portion 18 is generally in the form of a tubular structure, the width and length of which depends on the type of surgery being performed. Other factors include the accessibility of the surgical site, the dimensions of the surgical implant and the delivery device being utilized. For endoscopic or laparoscopic surgical procedures the endoscopic portion 18 is configured so as to allow insertion into a cannula. For example, if a 10mm cannula is being utilized for endoscopic positioning of the surgical implant the diameter of the endoscopic portion 18 cannot be greater than 10mm.

Figure 5:
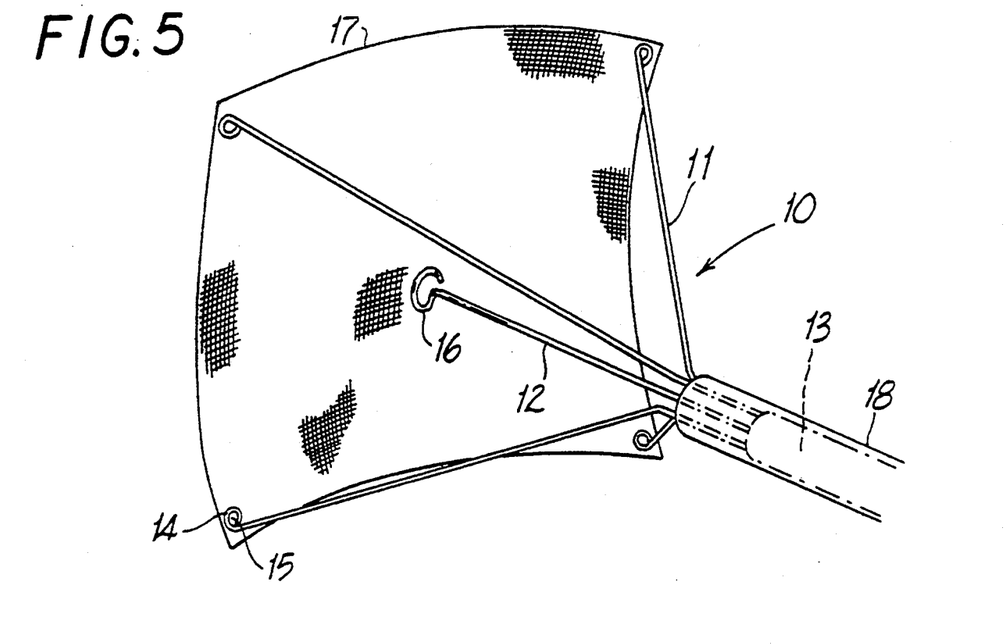
FIG. 5 is a perspective view of an embodiment of the present invention illustrating delivery arms secured to a mesh implant and a pusher rod creating a convexity in the mesh implant.
Figure 6:
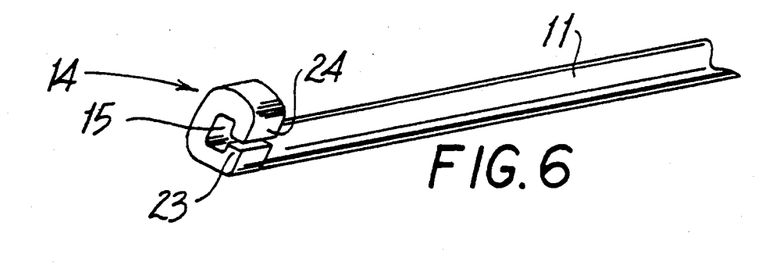
FIG. 6 is a perspective view of a distal end of a delivery arm constructed in accordance with an alternate embodiment of the present invention.

The delivery device 10 comprises a plurality of elongated delivery arms 11 which are preferably located at the distal end of an elongated rod 13 or other structure, shown in partial phantom in FIG. 5. In a preferred embodiment, the delivery arms 11 have a retaining means, such as eyelets 14, attached to or formed at the distal end of the delivery arms 11. These eyelets facilitate the securing of the delivery arms to the surgical mesh. The eyelets 14 may be formed or attached to the delivery arms, perpendicular to the delivery arm's longitudinal axis, parallel to the delivery arm's longitudinal axis or at any other angle to the longitudinal axis of the delivery arm sufficient to facilitate the securing of the surgical mesh. Additionally, the eyelets 14 may have a channel 23 between the outer wall 24 of the eyelet 14 and the eyelet aperture 15, as shown in FIG. 6. This allows a suture or other securing device to pass through the channel 23 to the aperture 15 instead of being threaded through the aperture.

Figure 7:
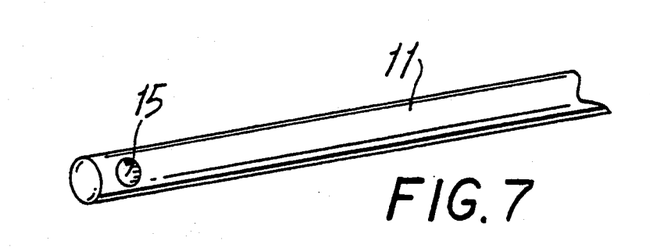
FIG. 7 is a perspective view of a distal end of a delivery arm constructed in accordance with another alternate embodiment of the present invention.

Referring to FIG. 7, the distal ends of the delivery arms (or retaining means) may be configured in other ways. For example, the delivery arms 11 may be elongated members which have an aperture 15 formed directly therein.

In still another embodiment the retaining means may be a cap attached to the distal end of each of the delivery arms, which facilitate the securing of the delivery arms to the surgical mesh. Generally, the distal end of the delivery arms or retaining means are configured so that they are able to be releasably secured to the surgical mesh by means of a securing device or suture. The number and length of the delivery arms may vary. The size of the implant and the type of surgical procedure being performed are factors to be considered when determining the number and length of the delivery arms.

Preferably, as shown in FIG. 1, the delivery arms 11 are positioned around the periphery of the surgical mesh and releasably secured thereto. However, the delivery arms may be positioned and releasably secured to the mesh in any configuration. The primary objective is that the arms are arranged to enable the surgical mesh to cover the surgical opening or wound.

An affecting means 12 may also be included at the distal end of the elongated rod 13. The affecting means is provided to affect or alter the shape of the surgical implant. For example, the affecting means may cause a surface of the surgical implant to concave or convex. The affecting means may be a rod or bar which applies pressure to or limits the pressure on the surgical implant. Alternately, the affecting means may be a device which causes one or more of the delivery arms to compress together or expand further apart so as to cause the shape of the surgical implant to alter. In one embodiment of the present invention, the affecting means comprises a pusher rod 12, as shown in FIG. 5. The pusher rod 12 is an elongated rod or other structure used to apply pressure to the surgical implant when in the extended or deployed position, thereby creating a convexity or limiting the concavity of the surgical mesh with respect to the endoscopic portion 18. The number and length of the pusher rod(s) may vary. For example, the size of the implant and the type of surgical procedure being performed are factors to be considered when determining the number and length of the pusher rod(s).

Figure 8:
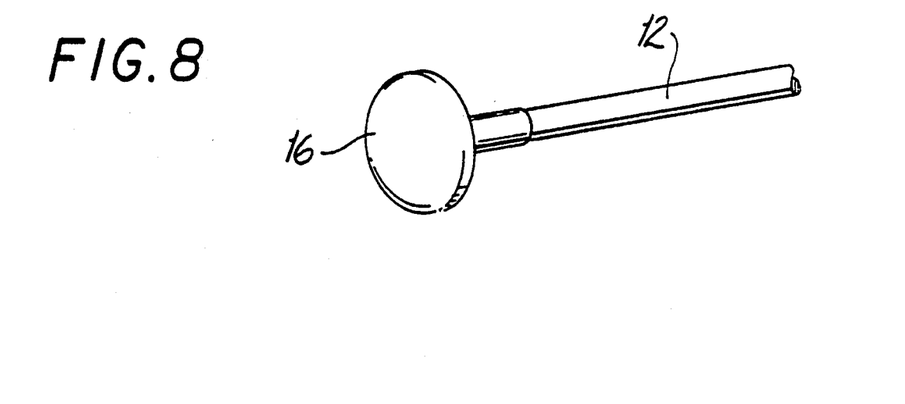
FIG. 8 is a perspective view of an alternate embodiment of a distal end of the pusher rod.

In a preferred embodiment the pusher rod 12 has a protective means 16 formed or attached to its distal end. Preferably, the protective means 16 is formed directly at the distal end of the pusher rod, as shown in FIG. 5. The protective member may be a frame-like or solid plate-like structure forming a spiral, circular, elliptical, square, rectangular, triangular, polyhedral, dome or irregular-shaped frame or plate. Additionally, the protective means may be "T", "H" or "Y" shaped. Alternatively, the protective means may include a cap 16, shown in FIG. 8. The cap 16 may have a flat, dome or ball shaped top or it may have any other irregular shaped surface which abuts the surgical mesh. However, other configurations for a protective member may come to the mind of those skilled in the art.

Figure 9:
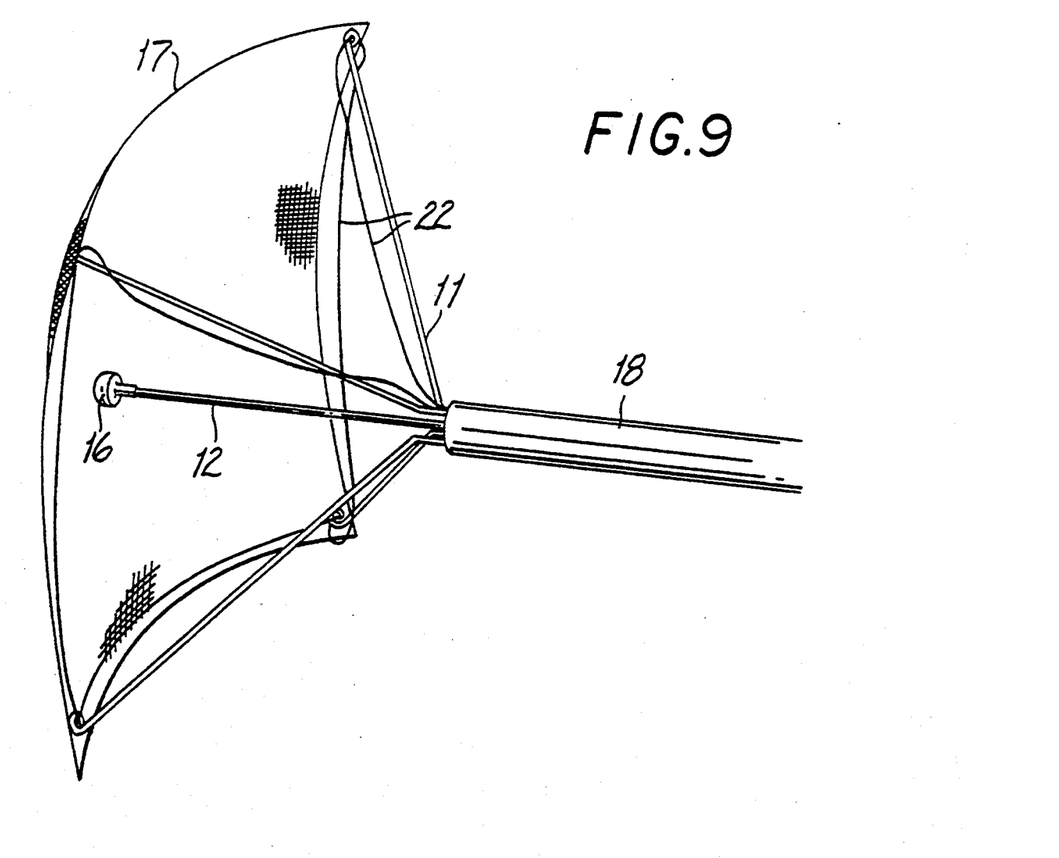
FIG. 9 is a perspective view of an alternate embodiment of the present invention illustrating a pusher rod and a suture releasably securing the delivery arms to the mesh implant.
Figure 10:
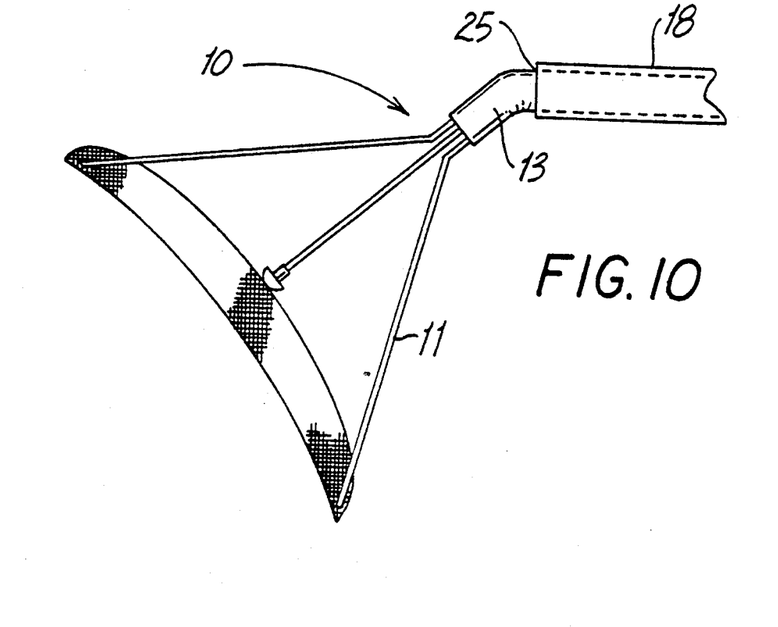
FIG. 10 is a side view of an embodiment of the present invention illustrating delivery arms secured to a mesh implant and a pusher rod limiting the degree of concavity of the surgical mesh.

Generally, the pusher rod 12 is arranged to apply pressure to the central area of the surgical implant 17, as shown in FIGS. 5 and 9, creating a convexity in the surgical mesh 17 with respect to the endoscopic portion 18. Such convexity is advantageous in endoscopic positioning of the surgical mesh in that it forces the surgical mesh against the body tissue. Alternatively, the pusher rod may be dimensioned and/or positioned to permit a predetermined degree of concavity of the surgical mesh, as shown in FIG. 10.

Figure 11:
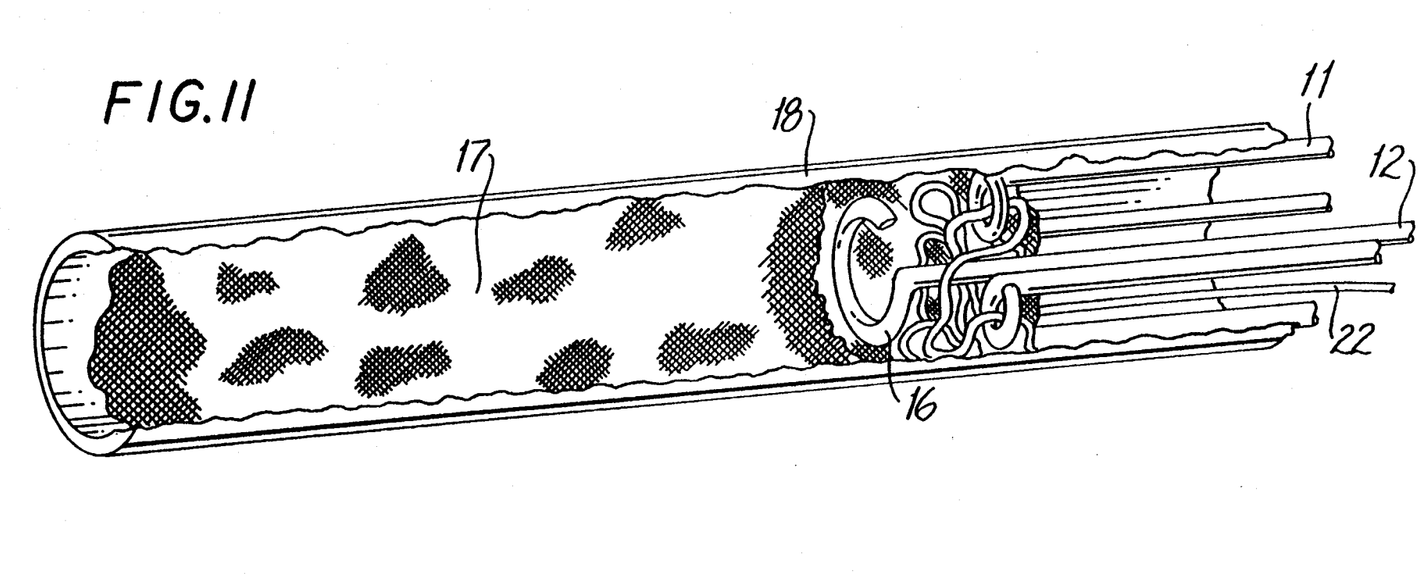
FIG. 11 is a perspective view in partial cutaway of the distal end of the endoscopic implant delivery device constructed in accordance an embodiment of the present invention.

Preferably, the delivery arms, and pusher rod if utilized, are fabricated from a resilient material. As shown in FIGS. 3 and 11, the use of resilient materials allows the surgical mesh 17, delivery arms 11, and pusher rod 12 to be compressed and retracted into the distal end of the endoscopic portion 18. The resilient nature of the material will allow the surgical mesh 17, the delivery arms 11, and the pusher rod 12 to assume a deployed position when extended out of the endoscopic portion 18 of the apparatus 30.

Figure 12:
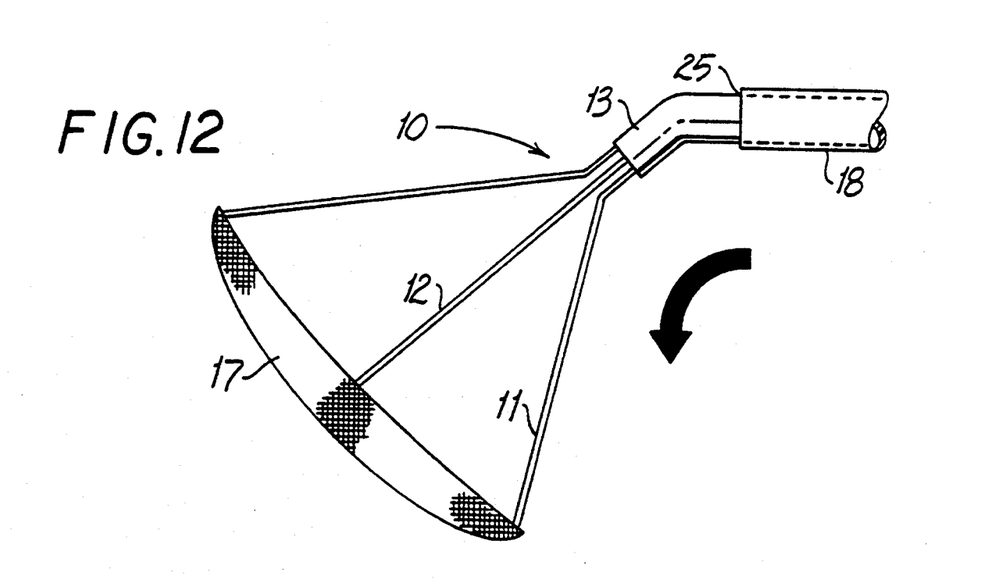
FIG. 12 is a side view of the distal end of an endoscopic implant delivery device with a deployed mesh implant affixed to a delivery device fabricated from an elastic material.

An articulating means may also be positioned at or adjacent to the distal end of the elongated rod. The articulating means is provided to bend or pivot the distal end of the elongated rod at an angle relative to the longitudinal axis of the elongated rod. Preferably, at least a portion of the distal end of the elongated rod 13 is fabricated from a resilient material. In this configuration, the rod 13 in its unstressed state, assumes an angle with respect to the longitudinal axis of the endoscopic portion 18 of the apparatus 30, as shown in FIG. 12. When the rod 13 is retracted into the endoscopic portion 18 of the apparatus 30, it cams against the distal end 25 of the endoscopic portion 18 and assumes a relatively straightened configuration within the endoscopic portion 18.

When the resilient portion of the rod 13 begins to extend beyond the distal end 25 of the endoscopic portion 18 the resilient nature of this portion of the rod causes the rod to begin to bend, as indicated by the arrow, changing the orientation of the delivery arms 11, pusher rod 12 and surgical mesh 17 with respect to the longitudinal axis of the endoscopic portion 18 or the proximal end of the elongated rod 13. As a greater portion of the resilient portion extends beyond the distal end 25 of the endoscopic portion 18, the angular orientation of the delivery arms 11, pusher rod 12 and surgical mesh 17 becomes greater. Ultimately, the rod 13 may extend out of the distal end 25 of the endoscopic portion 18 a distance sufficient to fully remove the stress from rod 13 whereupon the resilient material returns to its original unstressed configuration, providing the predetermined angular orientation of the delivery arms with respect to the longitudinal axis of the endoscopic portion 18 of the apparatus 30.

Employing a resilient material at the distal end of the rod 13 allows delivery of the surgical mesh at a desired orientation or pressing of the mesh against the body tissue making it easier for the surgeon to fasten the surgical mesh to the tissue. It also enables the surgeon to position the delivery device and surgical mesh in areas where a straight device would be difficult or inconvenient to use.

Although, the preferred articulating means utilizes shape-memory alloy, other means to cause the distal end of the elongated rod to bend or pivot are envisioned including, for example, mechanical linkages. Resilient materials contemplated for fabricating the delivery arms, pusher rod(s) and/or the resilient portion of the elongated rod are those that have spring-like properties and are capable of being deformed by an applied stress and then return, or recover, to their original shape or configuration when the stress is removed. The resilient material can be either polymeric or metallic or a combination thereof, however, it is preferred that it be highly resilient. For example, such resilient materials may include silicone, polyvinyl resins, polyethylene, resilient polyacetals, polyurethane, resilient polycetals, polyurethane, synthetic rubbers, teflon, tetrafluorethylene fluorocarbon polymer, spring-tempered steel, and spring tempered stainless steel. Shape-memory alloys also may be used for the resilient material. Shape-memory alloys which exhibit pseudoelastic or superelastic properties are preferred. Fundamentally, alloys which are capable of transforming between martensitic and austenitic shapes are able to exhibit shape-memory effect. The transformation between the martensitic and austenitic phases may be caused by temperature or stress.

In the case of pseudoelastic shape memory alloys, conditions may occur where temperature is not relied on to accomplish shape change. Further, pseudoelastic alloys may be elastically deformed far beyond the elastic limits of conventional metals. Suitable shape-memory alloys are described in U.S. Pat. No. 4,665,906.

The method for positioning surgical implants adjacent to body tissue comprises, releasably securing a surgical implant to a delivery device having retaining means formed at the distal end thereof, positioning the surgical mesh and delivery device adjacent to the body tissue, and releasing the surgical mesh from the delivery device by removing the securing device from the retaining means.

The surgical mesh may be secured to the delivery device by passing a suture or other securing device through the retaining means and at least partially through the surgical mesh. Preferably, a suture 22 is sequentially passed through the eyelet apertures 15 and at least partially through the surgical mesh while wrapping the suture around the eyelet 14 as shown in FIG. 9. In another embodiment the surgical mesh is secured to the delivery device by passing a suture 22 through the eyelet aperture 15 and at least partially through the surgical mesh 17 and tying the suture around the eyelet. This technique may be repeated to adequately secure the surgical mesh 17 to the delivery device 10 for the particular application of the implant.

While describing the securing device as a suture, it should be understood that other types of yarns, threads, fibers or filaments may be used as the securing device. In addition, the securing device may be any flexible or rigid member for securing the surgical mesh to the delivery device. Preferably, the securing device is positioned and/or constructed to allow removal thereof to facilitate release of the implant from delivery device.

Once the implant is secured to the delivery device and preferably retracted therein the delivery device is positioned adjacent to the operative body tissue. The delivery device may be positioned adjacent to the body tissue manually during conventional invasive surgical procedures. Preferably, however, for use with a hernia repair mesh an endoscopic instrument such as the apparatus of the present invention is utilized. As discussed above and referring to FIG. 1, delivery device 10 includes delivery arms 11 formed at the distal end of an elongated rod 13 which is releasably secured to the surgical mesh 17. The elongated rod 13 extends through an elongated tubular structure comprising the endoscopic portion 18 of the apparatus 30. Applying a force to the endoscopic portion 18 in the direction of the longitudinal axis of the rod 13 will cause the endoscopic portion 18 to slide coaxially with respect to rod 13 in the longitudinal direction so as to retract or extend the delivery arms. If the optional pusher rod 12 is utilized, it too will be retracted by or extended from the endoscopic portion 18 of the apparatus 30 upon coaxial proximal movement of the endoscopic portion 18.

Once in position, the surgical mesh is released from the delivery device by removing the securing device from the delivery arms. In a preferred embodiment, the securing device is a single suture or a plurality of sutures which are continuously threaded through the eyelet apertures as discussed above. The suture 22 is sequentially passed through each eyelet aperture 15, at least partially through the surgical mesh and is removed by pulling the suture sufficiently to release the surgical mesh from delivery arms. In an alternate embodiment, the suture 22 or sutures may extend into the endoscopic portion 18 of the instrument and either exit the instrument at the handle assembly 19 to allow manual removal of the suture, as shown in FIGS. 1 and 3, or the suture or sutures may be operatively connected to the handle assembly where a trigger or other actuating structure (not shown) causes withdrawal of the suture. Since, in the preferred embodiment, the suture is merely threaded through the eyelets and the mesh, the suture is easily pulled through the eyelet aperture and mesh, thereby sequentially releasing the surgical mesh from the delivery arms. Alternatively, the surgeon may remove the suture or securing device by manually cutting the suture or securing device using conventional cutting devices at one or more of the eyelets as required to release the mesh from the delivery device.

Once the securing device is removed, the mesh may be held in place by the delivery device pressing it against the body tissue. Alternatively, the mesh may be secured to the body tissue prior to removal of the securing device. The mesh may be secured to the body tissue by means of suture, clips and/or staples.

It will be understood that various modifications can be made to the embodiments of the present invention herein disclosed without departing from the spirit and scope thereof. For example, various sizes of the instrument are contemplated, as well as various types of construction materials. Also, various modifications may be made in the configuration of the parts. Therefore, the above description should not be construed as limiting the invention but merely as exemplifications of preferred embodiments thereof. Those skilled in the art will envision other modifications within the scope and spirit of the present invention as defined by the claims appended hereto.

What is claimed is:

1. Apparatus for positioning surgical implants adjacent to body tissue comprising:
   an elongated rod having a plurality of delivery arms secured to a distal end thereof for releasably receiving a peripheral portion of a surgical implant;
   securing means in contact with distal end of said delivery arms for detachably securing said surgical implant to said delivery arms; and
   pusher rod means secured to the distal end of said elongated rod for contacting and affecting tile shape of said surgical implant, said pusher rod means being configured to contact said surgical implant at an interior portion of said surgical implant spaced from said peripheral portion thereof, and said pusher rod having a protective member positioned at a distal end thereof for preventing the pusher rod means from contacting the surgical implant; said distal end of said pusher rod means being located at a position radially inwardly of said distal ends of said delivery arms;
   wherein upon deployment of said surgical implant, said delivery arms cause said peripheral portion of said surgical implant to expand and said pusher rod means contacts and affects the shape of said interior portion of said surgical implant.

2. Apparatus according to claim 1 further comprising:
   a handle portion; and
   elongated tubular structure having an endoscopic portion at a distal end thereof, a proximal end connected to said handle portion and receive at least a proximal portion of said elongated rod.

3. Apparatus according to claim 3 further comprising:
   trigger means pivotally connected to said handle portion and operatively connected to said elongated rod for effecting relative reciprocal coaxial movement of said elongated rod between a retracted and extended position with respect to said elongated tubular structure.

4. Apparatus according to claim 3 further comprising rotating means for rotating said elongated rod about its longitudinal axis relative to said handle portion.

5. Apparatus according to claim 2, further comprising a gripping means attached to said proximal end of said elongated tubular structure.

6. Apparatus according to claim 2 further comprising finger gripping means attached to said proximal end of said elongated tubular structure for facilitating reciprocating movement of said elongated tubular structure.

7. Apparatus according to claim 1 wherein said delivery arms have retaining means formed thereon.

8. Apparatus according to claim 7 wherein said retaining means comprises an eyelet.

9. Apparatus according to claim 1 wherein said delivery arms are fabricated from a resilient material.

10. Apparatus according to claim 9 wherein said resilient material is shape-memory alloy.

11. Apparatus according to claim 1 wherein a portion of said elongated rod is fabricated from a resilient material.

12. Apparatus according to claim 11 wherein said resilient material has an unstressed configuration at an angle with respect to a longitudinal axis of a proximal end of said elongated rod.

13. Apparatus according to claim 11 wherein said resilient material is shape-memory alloy.

14. Apparatus according to claim 1 wherein said securing means comprises a suture.

15. Apparatus according to claim 1 wherein said protective member comprises a loop formed at said distal end of said pusher rod means.

16. Apparatus according to claim 1 wherein said protective member comprises a cap attached to said distal end of said pusher rod means.

17. A method for positioning surgical implants adjacent to body tissue, comprising:
   providing a delivery device having an elongated rod with a plurality of delivery arms secured to a distal end thereof for releasably receiving a peripheral portion of an implantable sheet material, securing means in contact with distal ends of said delivery arms for releasably securing said peripheral portion of said implantable sheet material to said delivery arms, and pusher rod means secured to said distal end of said elongated rod for contacting and affecting the shape of an interior portion of said implantable sheet material, said pusher rod means contacting said implantable sheet material at a point spaced from the peripheral portion thereof, a distal end of said usher rod means being located at a position radially inwardly of said distal ends of said delivery arms; wherein upon positioning of said implantable sheet material, said delivery arms cause said peripheral portion of said implantable sheet material to expand and said pusher rod means contacts and affects the shape of said interior portion of said implant;
   releasably securing an implantable sheet material to said delivery arms;
   positioning said implantable sheet material and said delivery device adjacent to body tissue; and
   releasing said implantable sheet material from said delivery device.

18. Apparatus for positioning surgical implants adjacent to body tissue, comprising:
   an implantable sheet material;
   an elongated rod having a plurality of delivery arms secured to a distal end thereof;
   securing means in contact with distal ends of said delivery arms and securing a peripheral portion of said implantable sheet material to said delivery arms;
   a handle portion connected to a proximal end of said elongated rod;
   an elongated tubular structure coaxially receiving at least a proximal end of said elongated rod, said elongated tubular structure being adapted for relative reciprocal coaxial movement relative to said elongated rod to move said delivery arms between a retracted and extended position; and
   pusher rod means secured to said distal end of said elongated rod for contacting and affecting the shape of an interior portion of said implantable sheet material, said pusher rod means being secured to said distal end of said elongated rod to contact said implantable sheet material at said interior portion, a distal end of said pusher rod means being located at a position radially inwardly of said distal ends of said delivery arms;

wherein upon movement of said delivery arms to said extended position, said delivery arms cause said implantable sheet material to expand and said pusher rod means contacts and affects the shape of said interior portion of said implantable sheet material.

19. Apparatus for positioning surgical implants adjacent to body tissue comprising:

a handle;

an elongated rod connected with said handle and having a plurality of delivery arms secured to a distal end thereof for releasably receiving a peripheral portion of a surgical implant;

securing means in contact with distal ends of said delivery arms for detachably securing said surgical implant to said delivery arms;

a pusher rod sectored to the distal end of said elongated rod for contacting and affecting the shape of said surgical implant, said pusher rod being configured to contact said surgical implant at a point spaced from the peripheral portion thereof, a distal end of said pusher rod being located at a position radially inwardly of said distal ends of said delivery arms;

an elongated tubular member having an endoscopic portion at a distal end thereof, a proximal end connected to said handle, and a bore into which at least a proximal portion of said elongated rod is received;

trigger means pivotally connected to said handle and operatively connected to said elongated rod for effecting relative reciprocal coaxial movement of said elongated rod between a retracted and extended position with respect to said elongated tubular member; and rotating means for rotating said elongated rod about said longitudinal axis relative to said handle.

20. Apparatus for positioning surgical implants adjacent to body tissue comprising:

an elongated rod having a plurality of delivery arms secured to a distal end thereof for releasably receiving a peripheral portion of a surgical implant, wherein a portion of said elongated rod is fabricated from a resilient material having an tinstressed configuration at an angle with respect to a longitudinal axis of a proximal end of said elongated rod;

securing means in contact with distal ends of said delivery arms for detachably securing said surgical implant to said delivery arms; and pusher rod means secured to the distal end of said elongated rod for contacting and affecting the shape of said surgical implant, a distal end of said pusher rod being located at a position radially inwardly of said distal ends of said delivery arms; said pusher rod means being configured to contact said surgical implant at an interior portion of said surgical implant spaced from said peripheral portion thereof.

* * * * *